(12) United States Patent
Detweiler et al.

(10) Patent No.: US 11,534,216 B2
(45) Date of Patent: Dec. 27, 2022

(54) TENSIONER FOR A STERNAL CLOSURE STRAP DEVICE

(71) Applicant: Jace Medical, LLC, Warsaw, IN (US)

(72) Inventors: Jason F. Detweiler, Warsaw, IN (US); Scott Steffensmeier, Winona Lake, IN (US)

(73) Assignee: Jace Medical, LLC, Warsaw, IN (US)

( * ) Notice: Subject to any disclaimer, the term of this patent is extended or adjusted under 35 U.S.C. 154(b) by 198 days.

(21) Appl. No.: 16/877,956

(22) Filed: May 19, 2020

(65) Prior Publication Data

US 2020/0367950 A1 Nov. 26, 2020

Related U.S. Application Data

(60) Provisional application No. 62/850,613, filed on May 21, 2019.

(51) Int. Cl.
*A61B 17/82* (2006.01)
*A61B 17/88* (2006.01)
*A61B 17/84* (2006.01)

(52) U.S. Cl.
CPC .......... *A61B 17/823* (2013.01); *A61B 17/846* (2013.01); *A61B 17/8861* (2013.01)

(58) Field of Classification Search
CPC .............. A61B 17/8861; A61B 17/823; A61B 17/8869; A61B 17/8019; A61B 2017/681
See application file for complete search history.

(56) References Cited

U.S. PATENT DOCUMENTS 4,730,615 A 3/1988 Sutherland et al.
5,190,545 A 3/1993 Corsi et al.
(Continued)

FOREIGN PATENT DOCUMENTS

EP 0238219 A1 9/1987
EP 0597258 A1 5/1994
(Continued)

OTHER PUBLICATIONS

Extended European Search Report dated Feb. 5, 2021 for European Patent Application No. 20175773.9 (12 pages).
(Continued)

*Primary Examiner* — Amy R Sipp
(74) *Attorney, Agent, or Firm* — Schwegman Lundberg & Woessner, P.A.

(57) ABSTRACT

A handheld closing device for closing a bone closure device. The handheld closing device includes a main body portion with an end and a receiving member located at the end of the main body portion. The receiving member is configured for receiving the securing member of the bone closure device. The handheld closing device further includes a tightening member rotatably connected to the main body portion. The tightening member includes a receiving hole configured for receiving the strap of the bone closure device. The tightening member is configured for tightening the strap. The handheld closing device further includes a lever pivotally connected to the main body portion. The lever is configured for operably engaging with the securing member to position the securing member in its locked position.

20 Claims, 3 Drawing Sheets

(56) References Cited

U.S. PATENT DOCUMENTS

| | | | |
|---|---|---|---|
| 5,355,913 A * | 10/1994 | Green | A61B 17/823 140/123.6 |
| 5,356,412 A | 10/1994 | Golds et al. | |
| 5,356,417 A | 10/1994 | Golds | |
| 5,683,404 A | 11/1997 | Johnson | |
| 6,007,538 A | 12/1999 | Levin | |
| 7,588,576 B2 | 9/2009 | Teague et al. | |
| 8,414,594 B2 | 4/2013 | Berger et al. | |
| 10,307,193 B2 | 6/2019 | Garcia et al. | |
| 2010/0087837 A1 * | 4/2010 | Jaramillo | A61B 17/8861 606/144 |
| 2010/0274249 A1 | 10/2010 | Dell'Oca | |
| 2013/0261625 A1 | 10/2013 | Koch et al. | |
| 2015/0128384 A1 | 5/2015 | Breen, IV et al. | |
| 2017/0150996 A1 * | 6/2017 | Williams | A61B 17/7059 |
| 2020/0367949 A1 | 11/2020 | Detweiler et al. | |

FOREIGN PATENT DOCUMENTS

| | | |
|---|---|---|
| EP | 3116424 A2 | 1/2017 |
| EP | 3750497 A2 | 12/2020 |
| JP | 3106821 U | 11/2004 |
| WO | 2015/142588 A2 | 9/2015 |

OTHER PUBLICATIONS

"U.S. Appl. No. 16/877,655, Final Office Action dated May 27, 2022", 11 pgs.

"U.S. Appl. No. 16/877,655, Non Final Office Action dated Feb. 11, 2022", 9 pgs.

"U.S. Appl. No. 16/877,655, Response filed Jan. 26, 2022 to Restriction Requirement dated Dec. 7, 2021", 2 pgs.

"U.S. Appl. No. 16/877,655, Response filed May 11, 2022 to Non Final Office Action dated Feb. 11, 2022", 8 pgs.

"U.S. Appl. No. 16/877,655, Response filed Jul. 14, 2022 to Final Office Action dated May 27, 2022", 10 pgs.

"U.S. Appl. No. 16/877,655, Restriction Requirement dated Dec. 7, 2021", 6 pgs.

"European Application Serial No. 20175773.9, Partial European Search Report dated Oct. 29, 2020", 14 pgs.

"European Application Serial No. 20175773.9, Response filed Sep. 8, 2021 to Extended European Search Report dated Feb. 5, 2021", 15 pgs.

* cited by examiner

TENSIONER FOR A STERNAL CLOSURE STRAP DEVICE

CROSS REFERENCE TO RELATED APPLICATIONS

This is a non-provisional application based upon U.S. provisional patent application Ser. No. 62/850,613, entitled "STERNAL CLOSURE STRAP DEVICE", filed May 21, 2019, which is incorporated herein by reference.

BACKGROUND OF THE INVENTION

1. Field of the Invention

The present invention relates to bone fixation devices, and, more particularly, to sternal closure strap devices.

2. Description of the Related Art

Sternal fixation or closure devices are used to fix together portions of a sternum in a reapproximation medical procedure. Various surgical procedures require that the sternum is cut in half and separated before the desired surgical procedure(s) is conducted in the thoracic cavity. In so doing, the surgeon will conduct a partial or median sternotomy wherein a longitudinal incision is made in the sternum which then allows the portions, e.g. halves, of the sternum to be separated. After the surgical procedure(s) has been conducted, the sternum must be reapproximated using one or more sternal fixation devices to hold and secure the portions of the sternum together. Generally, each sternal fixation device will engage or otherwise wrap around the sternal portions in order to hold and secure the sternal portions together.

A typical sternal fixation device comprises a stainless-steel wire. In operation, the wire is wrapped around the sternal portions or weaved within through-holes in each sternal portion to form a loop that engages with both of the sternal portions. Thereafter, a separate tool, such as a tensioner, is required to twist the ends of the wire around one another to tighten the loop and secure the sternal portions together. Once the looped wired is sufficiently tight, another tool, such as a wire cutter, is required to cut the excess wire in order to reduce the overall profile of the sternal fixation device. Generally, it is a cumbersome process to hold the tensioner and operate the wire cutters at the same time. Furthermore, without designated tension indicators, the user of the various tools may under or over tighten the wire, which may damage the sternum and/or surrounding tissue. As can be appreciated, any damage to the sternum and/or surrounding tissue may cause a plethora of issues, including a partial or complete separation of the sternal portions.

What is needed in the art is an efficient and compact tool for holding and manipulating a bone fixation device.

SUMMARY OF THE INVENTION

The present invention provides a handheld and multipurpose closing device for temporarily holding, tensioning, and closing any desired bone closure strap device in order to securely hold juxtaposed bone portions together. The closing device generally includes a main body portion, a receiving member, and a tightening member rotatably connected to the main body portion. The tightening member includes a receiving hole configured for receiving the strap of the bone closure device. The tightening member is configured for tightening the strap. The closing device further includes a lever pivotally connected to the main body portion. The lever is configured for operably engaging with the securing member to position the securing member in its locked position.

The invention in one form is directed to a handheld closing device for closing a bone closure device. The bone closure device includes a strap and a securing member. The securing member has a locked position for securing the strap therein upon the strap being looped around bone portions to secure the bone portions. The handheld closing device includes a main body portion with an end and a receiving member located at the end of the main body portion. The receiving member is configured for receiving the securing member. The handheld closing device further includes a tightening member rotatably connected to the main body portion. The tightening member includes a receiving hole configured for receiving the strap of the bone closure device. The tightening member is configured for tightening the strap. The handheld closing device further includes a lever pivotally connected to the main body portion. The lever is configured for operably engaging with the securing member to position the securing member in its locked position.

The invention in another form is directed to a method of closing a bone closure device to secure bone portions. The bone closure device includes a strap and a securing member. The securing member has a locked position for securing the strap therein. The method includes an initial step of providing a handheld closing device. The handheld closing device includes a main body portion with an end and a receiving member located at the end of the main body portion. The receiving member is configured for receiving the securing member. The handheld closing device further includes a tightening member rotatably connected to the main body portion. The tightening member includes a receiving hole configured for receiving the strap of the bone closure device. The handheld closing device further includes a lever pivotally connected to the main body portion. The lever is configured for operably engaging with the securing member. The method includes the further steps of positioning the securing member within the receiving member and looping the strap around the bone portions. The method includes the further steps of threading the strap through the securing member and threading the strap through the receiving hole of the tightening member. The method includes the further steps of tightening the strap by rotating the tightening member and actuating the lever to position the securing member in its locked position for securing the bone portions.

An advantage of the present invention is that the handheld closing device combines the functions of tightening and securing the strap within the securing member, which then allows a user to efficiently tighten the strap to a desired and indicated tension and subsequently position the securing member in its locked position to fix the strap to the securing member with the same compact tool.

Another advantage of the present invention is that the handheld closing device allows a user to preposition and retain the securing member of the bone closure device within the handheld closing device, which provides for a more efficient reapproximation of the sternum.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates an embodiment of the invention, in one form, and such exemplification is not to be construed as limiting the scope of the invention in any manner.

DETAILED DESCRIPTION OF THE INVENTION

Figure 1:
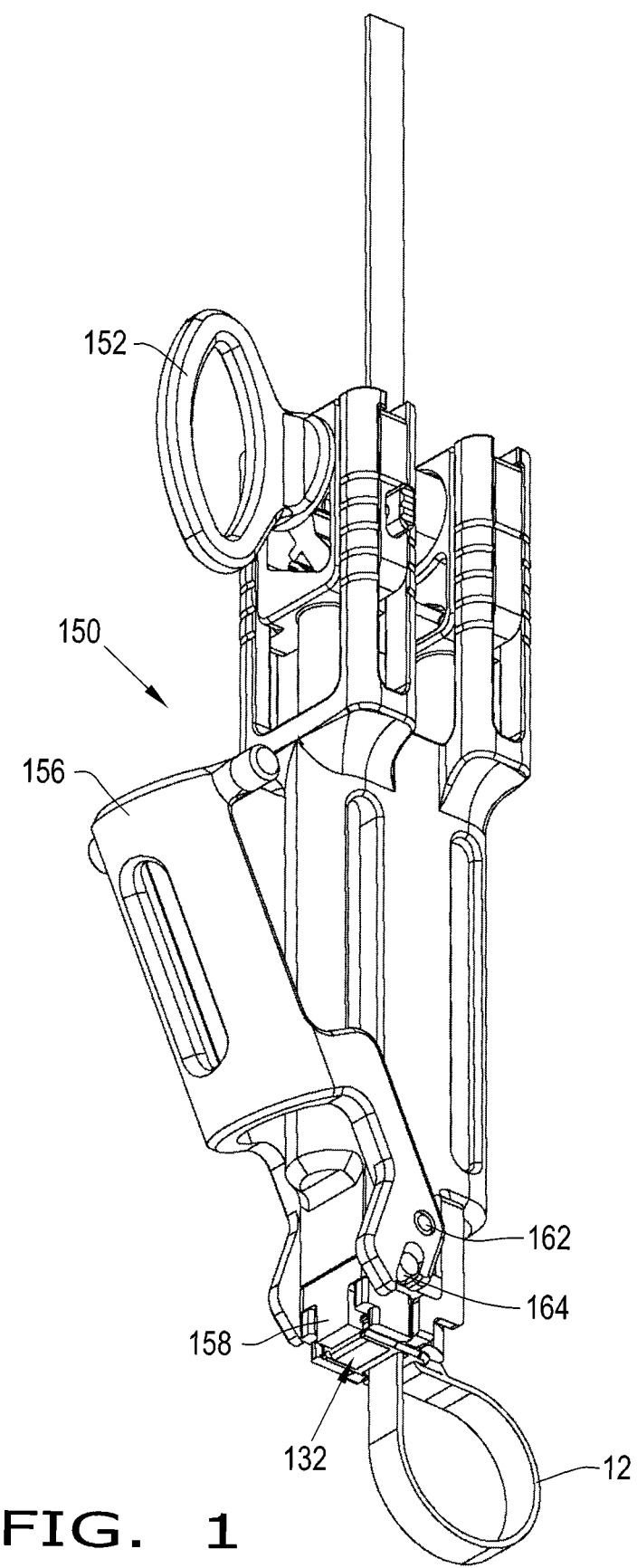
FIG. 1 is a perspective view of an embodiment of a handheld closing device for temporarily holding a securing member, tensioning or tightening the strap of the securing member, and closing the securing member in order to securely hold juxtaposed bone portions together.
Figure 2:
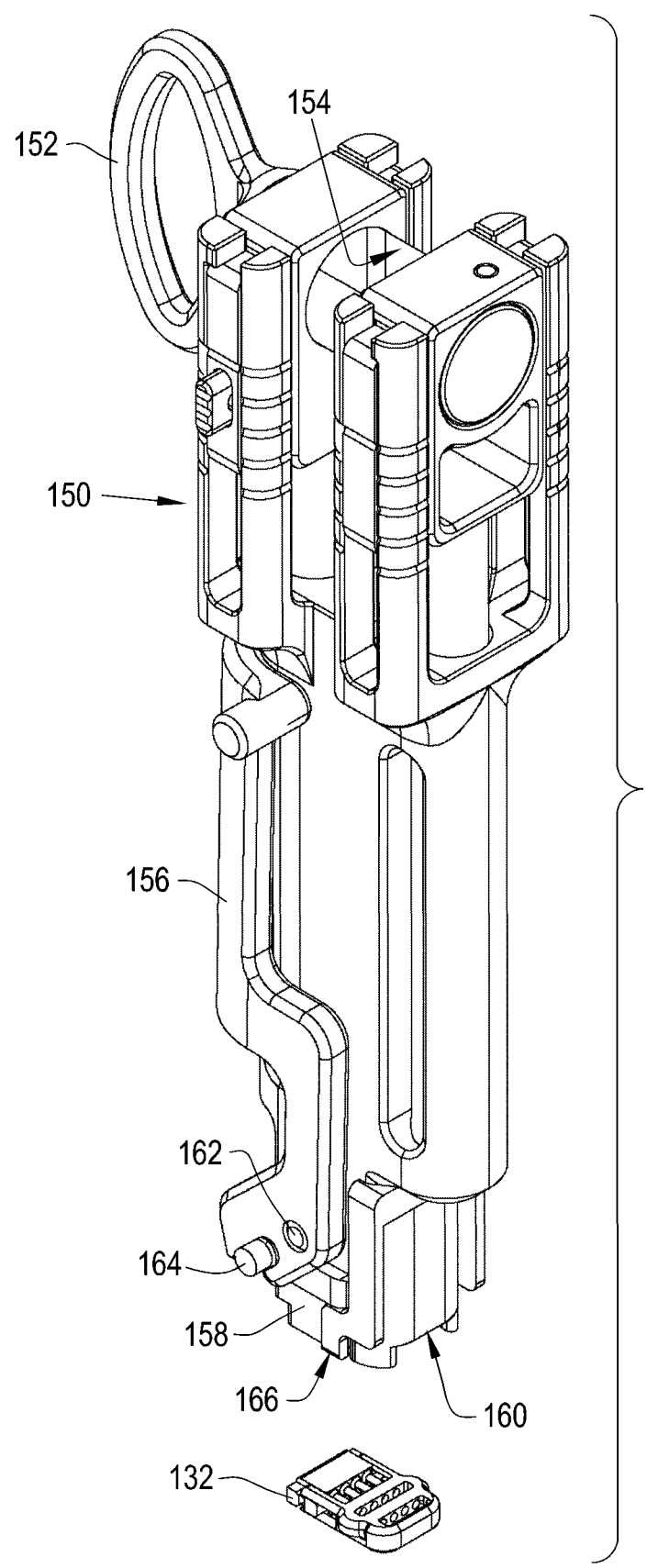
FIG. 2 is an exploded view of the handheld closing device of FIG. 1.
Figure 3:
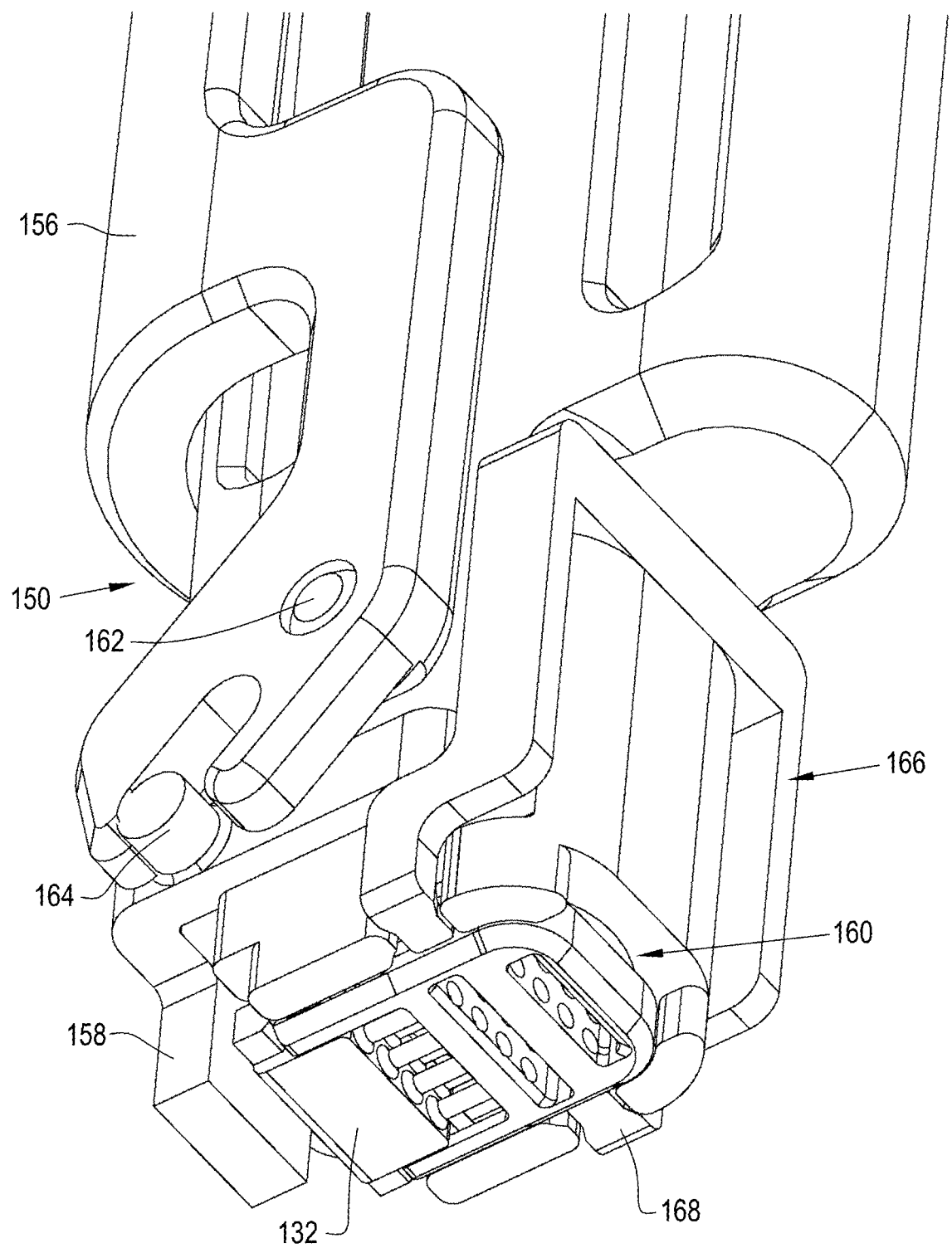
FIG. 3 is a bottom perspective view of the handheld closing device of FIGS. 1-2.

Referring now to the drawings, and more particularly to FIGS. 1-3, there is shown an embodiment of a handheld closing device 150. The handheld closing device 150 may be in the form of a handheld and multipurpose tensioner 150 for temporarily holding, tensioning or tightening, and closing any desired bone closure strap device in order to securely hold juxtaposed bone portions, for example halves of a sternum, together. For example, the handheld closing device 150 may be used to manipulate a two-part securing member 132, as described in U.S. patent application Ser. No. 16/877,655, which is incorporated herein by reference. Therein, the handheld closing device 150 may temporarily hold the securing member 132, tension a strap 12 through the securing member 132, and close the securing member 132 to secure the strap 12 within the securing member 132.

The handheld closing device 150 may generally include a tightening member 152 with a receiving hole 154 for receiving the strap 12, a lever 156, a movable end tab 158 that is actuated by the lever 156, and a receiving member 160, e.g. recess 160, for receiving the securing member 132 (FIG. 2). The handheld closing device 150 may be positioned in between an unlocked position in which the lever 156 rests against the main body portion of the handheld closing device 150 (FIG. 2) and a locked position in which the lever 156 is actuated and the end tab 158 manipulates the securing member 132 to secure the strap 12 within the securing member 132 (FIG. 1). For instance, in the locked position of the handheld closing device 150, the end tab 158 may engage and slide one portion of the securing member 132 into another portion of the securing member 132 in order to position the securing member 132 in its locked position to fix the strap within the securing member 132. It should be appreciated that the handheld closing device 150, including any component thereof, may be composed of any desired material, such as metal and/or plastic.

The tightening member 152 may be rotatably and slidably connected to the body of the handheld closing device 150. Once the strap 12 is threaded through the interior cavity in the main body portion and the receiving hole 154 of the tightening member 152, the tightening member 152 may be rotated or twisted to wrap the strap 12 around the middle portion of the tightening member 152. Hence, the looped strap 12 becomes shortened to temporarily hold the halves of the sternum together. The tightening member 152 may be in the form of an eye-bolt or knob with the receiving hole 154 being a slot through the middle portion of the eye-bolt. The tightening member 152 may also vertically translate, e.g. move up and down, relative to the main body portion. For instance, the tightening member 152 may slide within designated tracks of the main body portion. Such vertical translation of the tightening member 152 may tighten the looped strap 12, loosen the looped strap 12, and/or indicate a tension of the looped strap 12. For instance, the handheld closing device 150 may further include a scale with one or more markings located near the top of the handheld closing device 150 for indicating the various levels of tension applied to the looped strap 12. Thus, as the user twists the tightening member 152, the looped strap 12 becomes shortened, which applies a downward force onto the tightening member 152. This force from the strap 12 causes the tightening member 152 to distally translate, e.g. slide downwardly, along its tracks. As the tightening member 152 slides downwardly, its position along the scale indicates a greater amount of force or tension which is being applied to the looped strap 12. As can be appreciated, the tightening member 152 may be biased by one or more biasing members, such as springs, for upwardly biasing the tightening member 152. Furthermore, as can be appreciated, the tracks may have one or more indexed positions which retain the tightening member 152. It should be appreciated that the tightening member 152 may have a release feature, such as a release button, which is operable to unwind the tightening member 152 and/or reset the position of the tightening member 152 within the body of the handheld closing device 150.

The lever 156 may be pivotally connected to the main body portion of the handheld closing device 150 at pivot 162. The lever 156 may be operably engageable with the securing member 132, by way of the end tab 158, to selectively position the securing member 132 in its locked position for securing the strap 12 within the securing member 132. The lever 156 may include engagement features, for example arms with angled recesses that are located below the pivot 162, which engage with and move the end tab 158.

The end tab 158 may be movably connected to the distal end of the main body portion of the handheld closing device 150. For instance, the end tab 158 may be slidably and/or pivotally connected to the main body portion. The end tab 158 may include an upper portion movably connected to the main body portion and a lower portion that selectively contacts the securing member 132. The end tab 158 may also be movably connected to the lever 156. For instance, the end tab 158 may include a pair of protrusions or nubs 164 that movably engage with the lever 156. The nubs 164 may engage with the corresponding recesses of the lever 156. Hence, as the lever 156 pivots, the lever 156 engages with the nubs 164 and moves the bottom tab 158, which in turn closes the securing member 132. The force of the lever 156 acting on the nubs 164 may slide the end tab 158 and/or otherwise move the end tab 158 downwardly and inwardly to manipulate a position of the securing member 132. It should be appreciated that the end tab 158 may engage with and move one portion, for example the male portion, of the securing member 132.

The handheld closing device 150 may also include a retaining member 166 for at least partially retaining the securing member 132 (FIG. 3). The retaining member 166 may be connected to the end of the main body portion of the handheld closing device 150, adjacent to the recess 160. Hence, the retaining member 166 and the recess 160 may be located at the distal end of the main body portion of the handheld closing device 150. The retaining member 166 may prevent the lateral migration of the securing member 132 during tensioning of the strap 12 and may also prevent the distal migration of the securing member 132 relative to the distal end of the handheld closing device 150. In more detail, the retaining member 166 may be in the form of a rail member with a pair of arms or rails 168 extending downwardly for contacting the sides of the securing member 132, for example the sides of the female portion of the securing member 132 (FIG. 3). The arms 168 of the retaining member 166 may be at least partially deformable such that the arms 168 outwardly deflect when positioning the securing member 132 into the recess 160 and inwardly revert to at least partially hold the securing member 132 in the recess 160. In this regard, the securing member 132 may be snap-fitted within the recess 160 via the retaining member 166. Thus, the arms 168 of the retaining member 166 prevent the securing member 132 from distally migrating, such as dropping out of the recess 160.

In operation, a user may perform a method of closing a bone closure device using the handheld closing device 150. Firstly, the user may position the handheld closing device 150 in its unlocked position (FIG. 2). The user may then position the securing member 132 within the handheld closing device 150. For instance, the user may snap-fit the securing member 132 into the recess 160 via the retaining member 166. Next, the user may subsequently thread the strap 12 around juxtaposed bone portions, forming a loop therearound, and through both of the securing member 132 and the handheld closing device 150. In more detail, the strap 12 may be threaded through the receiving hole 154 of the tightening member 152. Thereafter, the user may twist the tightening member 152 in order to wrap the strap 12 around the tightening member 152. Due to the tension on the strap 12, the tightening member 152 may downwardly slide to indicate a level of tension on the strap 12, which also correlates to the tension on the bone portions. Once the appropriate tension on the strap 12 has been obtained, the user may position the handheld closing device 150 in its locked position by actuating the lever 156. The lever 156 then moves the end tab 158 so that the end tab 158 engages with and slides one portion of the securing member 132 into another portion of the securing member 132 in order to position the securing member 132 in its locked position. By way of the locked position of the securing member 132, the strap 12 becomes fixed within the securing member 132 which maintains the desired amount of tension on the strap 12. Once the securing member 132 is in its locked position, the strap 12 may be removed from the handheld closing device 150. As can be appreciated, any excess amount of the strap 12 may be removed in order to reduce the overall profile of the bone closure device. Then, after the securing member 132 is set in place, the handheld closing device 150 may be repositioned into its unlocked position and/or sterilized for subsequent use.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A handheld closing device for closing a bone closure device, the bone closure device including a strap and a strap securing member, the strap securing member having a locked position for securing the strap therein upon the strap being looped around bone portions to secure the bone portions, the handheld closing device comprising:
   a main body portion including a distal end;
   a receiving member located at the distal end of the main body portion, the receiving member being configured for receiving the strap, securing member;
   a tightening member rotatably connected to the main body portion, the tightening member including a receiving hole configured for receiving the strap of the bone closure device, the tightening member being configured for tightening the strap;
   a lever pivotally connected to the main body portion along a pivot axis that extends through the main body portion proximate the distal end of the main body portion, the lever including a first arm and a second arm through which the pivot axis extends, the lever being configured for operably engaging with the strap securing member to position the strap securing member in the locked position; and
   an end tab movably connected to the main body portion and the lever, the end tab being configured for engaging with the strap securing member and moving the strap securing member upon actuation of the lever, wherein the end tab includes a first nub and a second nub that are slidably received in a first angled recess in the first arm of the lever and a second angled recess in the second arm of the lever, respectively, for moveably engaging with the lever, the first angled recess and the second angled recess located distally of the pivot axis in the first arm and the second arm, respectively.

2. The handheld closing device of claim 1, wherein, upon actuation of the lever, a force of the lever acting on the first nub and the second nub is able to move the end tab in a distal direction relative to the main body portion and in a lateral direction toward the strap securing member.

3. The handheld closing device of claim 1, further comprising a retaining member for removably retaining the strap securing member in the receiving member.

4. The handheld closing device of claim 3, wherein the retaining member is connected to the distal end of the main body portion and is located adjacent to the receiving member, the retaining member being configured for engaging with the strap securing member to prevent a movement of the strap securing member.

5. The handheld closing device of claim 3, wherein the retaining member includes a pair of arms for engaging with the strap securing member.

6. The handheld closing device of claim 5, wherein the pair of arms of the retaining member are at least partially deformable such that the pair of arms outwardly deflect upon positioning the strap securing member within the receiving member and inwardly revert to hold the strap securing member within the receiving member.

7. The handheld closing device of claim 1, wherein the receiving member is in the form of a recess.

8. The handheld closing device of claim 1, wherein the tightening member has a middle portion, and wherein the receiving hole is located in the middle portion of the tightening member such that upon rotating the tightening member the strap wraps around the middle portion of the tightening member to tension the strap.

9. The handheld closing device of claim 8, wherein the tightening member is further slidably connected to the main body portion, the tightening member being further configured for vertically translating for indicating a tension of the strap.

10. The handheld closing device of claim 8, wherein the tightening member is in the form of an eye-bolt.

11. A handheld closing device for closing a bone closure device, the bone closure device including a strap and a strap securing member, the strap securing member having a locked position for securing the strap therein upon the strap being looped around bone portions to secure the bone portions, the handheld closing device comprising:
- a main body portion including a distal end;
- a receiving member located at the distal end of the main body portion, the receiving member being configured for receiving the strap securing member;
- a tightening member rotatably connected to the main body portion, the tightening member including a receiving hole configured for receiving the strap of the bone closure device, the tightening member being configured for tightening the strap;
- a lever pivotally connected to the main body portion proximate the distal end of the main body portion, the lever being configured for operably engaging with the strap securing member to position the strap securing member in the locked position; and
- an end tab movably connected to the main body portion and the lever, the end tab being configured for engaging with the strap securing member and moving the strap securing member upon actuation of the lever, wherein, upon actuation of the lever, a force of the lever acting on the end tab is able to move the end tab in a distal direction relative to the main body portion and in a lateral direction toward the strap securing member.

12. The handheld closing device of claim 11, wherein the end tab includes at least a first protrusion that slidably engages with the lever.

13. The handheld closing device of claim 12, wherein the end tab includes a second protrusion that slidably engages with the lever.

14. The handheld closing device of claim 13, wherein the first protrusion is slidably received in a first recess in the lever, and the second protrusion is slidably received in a second recess in the lever.

15. The handheld closing device of claim 14, wherein the lever is pivotally connected to the main body portion along a pivot axis that extends through the lever and through the main body portion proximate the distal end of the main body portion.

16. The handheld closing device of claim 15, wherein the first recess and the second recess are located distally of the pivot axis along the lever.

17. The handheld closing device of claim 11 further comprising a retaining member for removably retaining the strap securing member in the receiving member.

18. The handheld closing device of claim 17, wherein the retaining member includes a pair of arms for engaging with the strap securing member.

19. The handheld closing device of claim 18, wherein the pair of arms of the retaining member are at least partially deformable such that the pair of arms outwardly deflect upon positioning the strap securing member within the receiving member and inwardly revert to hold the strap securing member within the receiving member.

20. The handheld closing device of claim 11, wherein the tightening member has a middle portion, and wherein the receiving hole is located in the middle portion of the tightening member such that upon rotating the tightening member the strap wraps around the middle portion of the tightening member to tension the strap.

* * * * *

UNITED STATES PATENT AND TRADEMARK OFFICE
CERTIFICATE OF CORRECTION

PATENT NO. : 11,534,216 B2
APPLICATION NO. : 16/877956
DATED : December 27, 2022
INVENTOR(S) : Detweiler et al.

It is certified that error appears in the above-identified patent and that said Letters Patent is hereby corrected as shown below:

In the Claims

In Column 6, Line 6, in Claim 1, delete "strap," and insert --strap-- therefor

In Column 6, Line 28, in Claim 1, delete "moveably" and insert --movably-- therefor Signed and Sealed this
Twenty-eighth Day of March, 2023

Katherine Kelly Vidal
Director of the United States Patent and Trademark Office